US00PP27245P3

(12) United States Plant Patent
Olesen

(10) Patent No.: US PP27,245 P3
(45) Date of Patent: Oct. 11, 2016

(54) CLIMBING ROSE PLANT NAMED 'POULCY028'

(50) Latin Name: ***Rosa* hybrid**
Varietal Denomination: Poulcy028

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 106 days.

(21) Appl. No.: 14/121,270

(22) Filed: Aug. 15, 2014

(65) Prior Publication Data

US 2016/0050802 P1 Feb. 18, 2016

(51) Int. Cl.
*A01H 5/02* (2006.01)

(52) U.S. Cl.
USPC ..... Plt./111

(58) Field of Classification Search
USPC ..... Plt./111, 134, 104, 145
See application file for complete search history.

(56) References Cited

PUBLICATIONS

Poulsen Roser A/S Courtyard Perfection by Poulsen Climbers Main varieties 2013, retrieved on Jan. 12, 2016, retrieved from the Internet at <http://www.poulsenroser.dk/media/73071/COURT-YARD-Climbers-2013_LR_Poulsen-Roser.pdf> one page.*

* cited by examiner

*Primary Examiner* — June Hwu

(57) ABSTRACT

A new garden rose plant of the Climbing class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulcy028'.

SUMMARY OF THE INVENTION

The present invention constitutes a new and distinct variety of garden rose plant of the Climbing rose class, specifically for compact flowering columns, which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulcy028', originated as a single seedling from the stated cross.

The new variety may be distinguished from its male pollen parent and female seed parent by the following characteristics. The female seed parent has orange blend flowers, while the new variety has yellow flowers. The male pollen parent is a ground cover rose, while the new plant is a climbing rose.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance; and
4. Consistent flowers from the top of the plant to the lower branches.

This combination of qualities is not present in previously available commercial cultivars of this type, known to the inventor, and distinguish 'Poulcy028' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcy028' was selected in the spring of 2004 by the inventor as a single plant from the progeny of the aforementioned hybridization.

Asexual reproduction of 'Poulcy028' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcy028' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy028'.

Specifically illustrated in FIG. 1 are stems, leaves, open flowers, with petals and petals detached, flower buds, and detached sepals showing the receptacle.

DETAILED DESCRIPTION OF THE VARIETY

Figure 1:
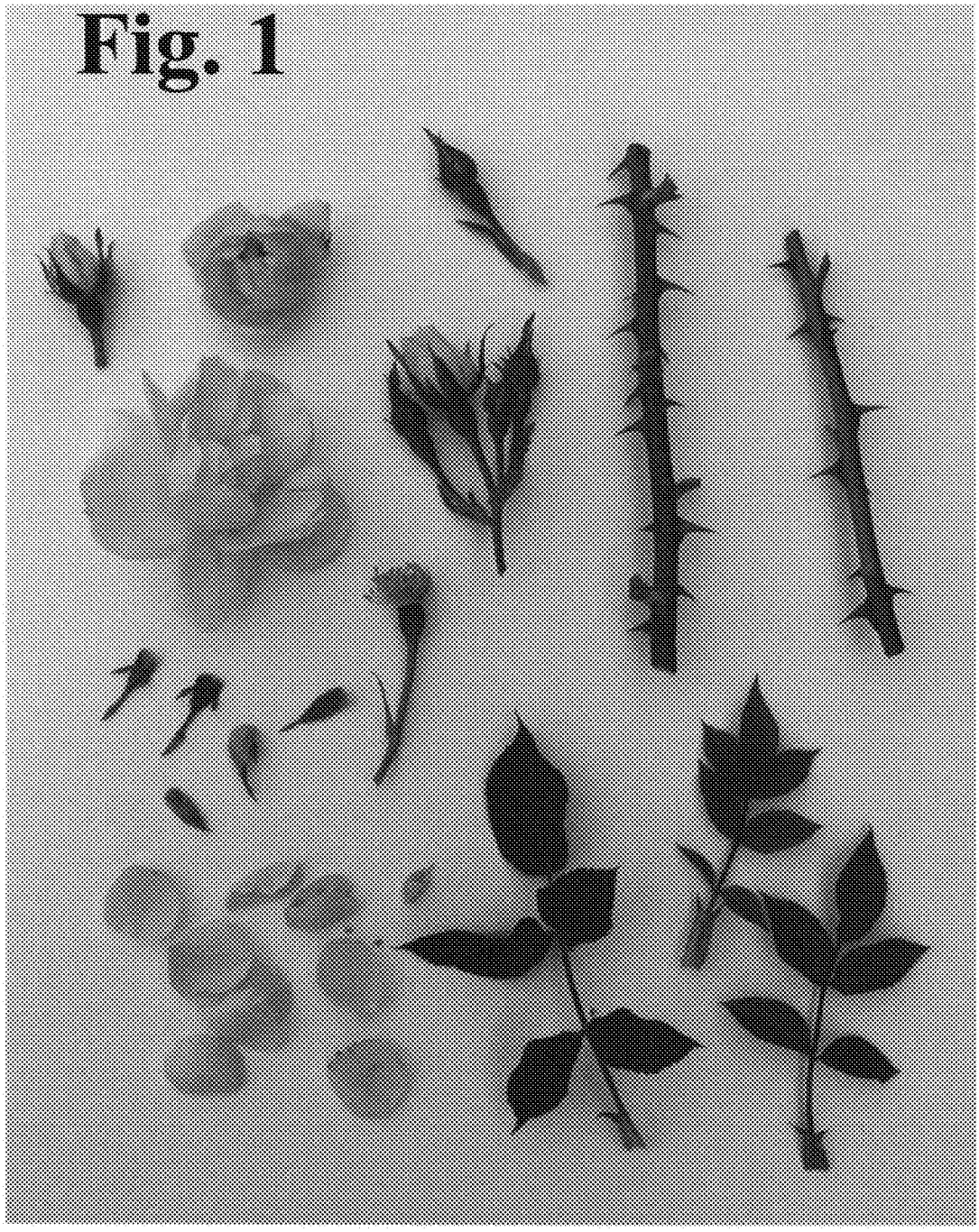
Figure 2:
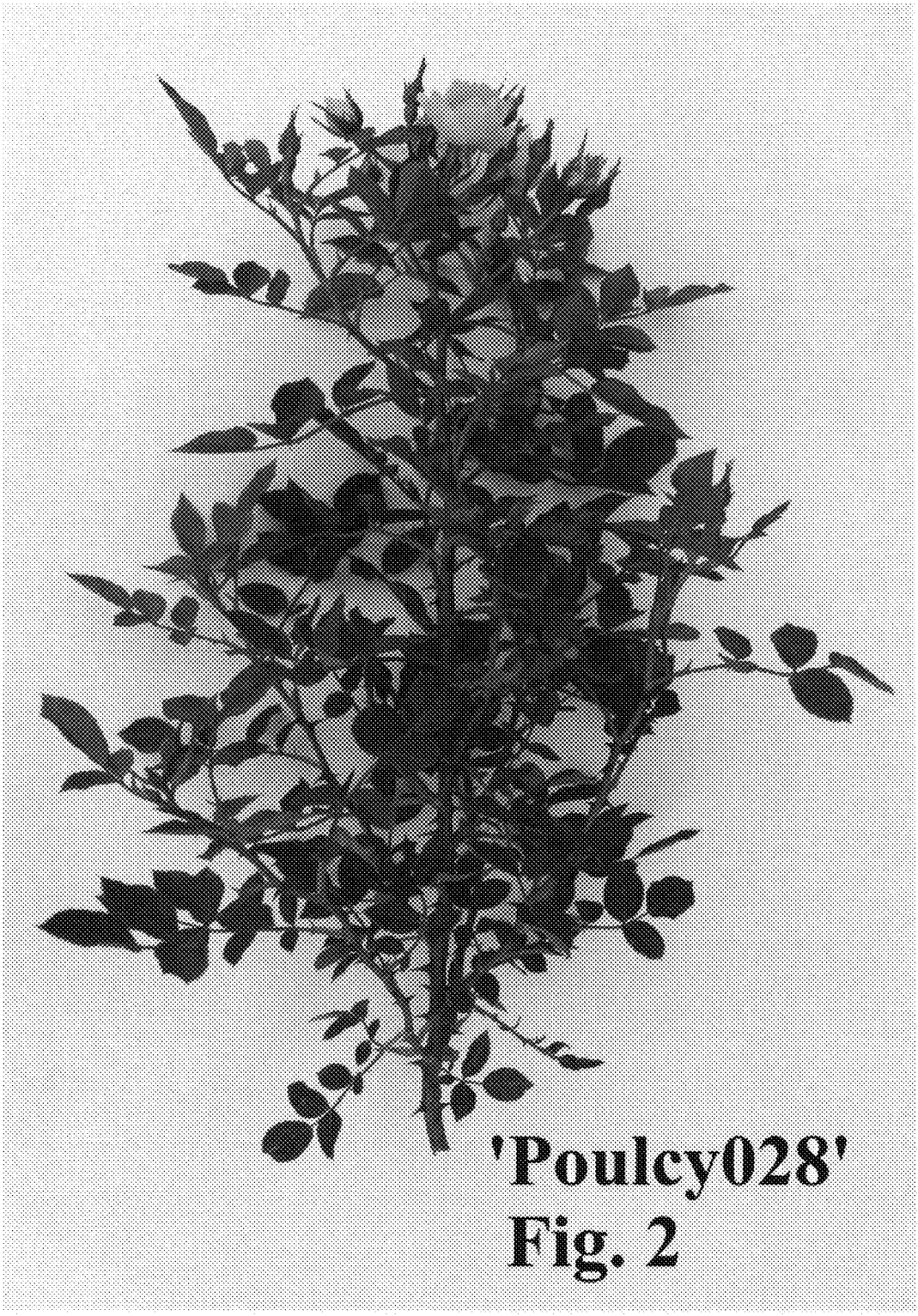
FIG. 2 shows a flowering branch. Plants shown are 2 years of age.

The following is a description of 'Poulcy028', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulyc003', U.S. Plant Pat. No. 15,106 are compared to 'Poulcy028' in Chart 1.

CHART 1

| | 'Poulcy028' | 'Poulyc003' |
|---|---|---|
| Petal Count | 25 petals | 70-80 petals |
| Flower Diameter | 55 mm | 40 mm |
| General Tonality of Flower Color | Yellow Group 13A | Yellow-Orange Group 14D |

FLOWER AND FLOWER BUD

Blooming habit: Continuous.

Flower bud:

*Size.*—Upon opening, 20 mm in length from base of receptacle to end of bud. Bud diameter is 8 mm.

*Bud form.*—Ovoid.

*Bud color.*—As sepals divide petals are Yellow-Orange Group 15C with occasional streaks the color of Red Group 43B.

*Sepal inner surface.*—Color: Yellow-Green Group 148B. Surface: Lightly pubescent.

*Sepal outer surface.*—Color: Yellow-Green Group 144A with intonations of Greyed-Purple Group 184A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—20 mm long, 8 mm wide.

*Receptacle.*—Texture: Smooth. Size: 8 mm in height, 5 mm wide. Color: Yellow-Green Group 144A with anthocyanin Greyed-Purple Group 183A.

*Shape.*—Campanulate.

*Pedicel.*—Surface Texture: Smooth. Length: 15 mm. Diameter: 2 mm on average. Color: Yellow-Green Group 144B with light intonations of Greyed-Red Group 182B. Strength: Strong.

*Peduncle.*—Length: 5 to 15 cm. Diameter: 3 mm. Color: Yellow-Green Group 144A. Texture: Smooth.

Flower bud development: Flower buds are borne singly and in clusters of about 5 flower buds per stem in panicle form, 15 to 20 cm in diameter. Reduced apical dominance in flower habit causes flower buds develop more evenly from the base of the plant to the upper branches than other climbing roses.

Flower bloom:

*Fragrance.*—Moderate floral.

*Duration.*—The blooms have a duration on the plant of approximately 7 to 10 days. Petals fall cleanly away from plant after flowers have fully matured.

*Size.*—Flower diameter is 55 mm when open. Flower depth is 25 mm.

*Flower shape.*—Semi-double flower with petals that curve out from the center. Initially flowers are somewhat globose. After opening, flower form is less formal.

*Shape of flower, side view.*—The upper portion is rounded. The lower portion is convex.

Petalage: Under normal conditions, flowers have 25 petals total, about 3 of which are petaloids.

General tonality of flower: Open flowers are Yellow Group 13A becoming Yellow Group 8C as the flowers mature.

Petal color:

*Upon opening, outer and inner petals.*—Upper surface: Yellow Group 13B. Lower surface: Yellow-Orange Group 14C.

*After opening, outer and inner petals.*—Upper surface: Yellow Group 8C. Lower surface: Yellow Group 8C.

*Basal petal spots.*—No distinctive coloration at the petal base observed.

Petals:

*Petal reflex.*—Flat.

*Margin.*—Entire and uniform. No undulations.

*Shape.*—Generally rounded. Apex shape: Rounded. Base shape: Rounded.

*Size.*—25 mm (1)×25 mm (w).

*Texture.*—Smooth.

*Thickness.*—Average.

Petaloids:

*Size.*—12 mm (1) by 8 mm (w).

*Quantity.*—About 3.

*Shape.*—Elliptical and irregular.

*Color.*—Same as petals.

Reproductive organs:

*Pollen.*—None observed.

*Anthers.*—Size: 2 mm in length. Color: Yellow Group 12D. Quantity: 28 on average.

*Filaments.*—Color: Orange Group 24B. Length: 5 mm.

*Pistils.*—Length: 5 mm. Quantity: 20 on average.

*Stigmas.*—Color: Greyed-Yellow Group 160B.

*Styles.*—Color: Greyed-Yellow Group 160B.

*Location of stigmas.*—Inferior in location relative to the length of the filaments and the height of the anthers.

*Hips.*—None Observed.

PLANT

Plant growth: Upright, bushy. Plants are 125 cm in height, and 100 cm wide.

Stems:

*Color.*—Juvenile growth: Yellow-Green Group 144B with anthocyanin Greyed-Red Group 182B. Mature growth: Yellow-Green Group 146B.

*Length.*—On average, canes are 30 to 40 cm from the base of the plant to the flowering portion.

*Diameter.*—6 mm.

*Internodes.*—On mature canes, there is an average distance of 25 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 7 mm.

*Shape.*—Upper portion is linear. Lower portion is concave.

*Color.*—Juvenile prickles: Greyed-Purple Group 187C. Mature prickles: Greyed-Red Group 179B and Greyed-Red Group 181A distinctly.

Plant foliage:

*Compound leaf.*—110 mm (1)×65 (w).

*Quantity.*—3 leaves per 10 cm of stem on average.

*Leaf bearing angle to the stem.*—45 degrees.

*Color of juvenile foliage.*—Upper side: Yellow-Green Group 146A with margins the color of Greyed-Purple Group 185A. Lower side: Yellow-Green Group 146B.

*Color of mature foliage.*—Upper side: Yellow-Green Group 146A. Lower side: Yellow-Green Group 146B.

Plant leaves and leaflets:

*Stipules.*—Size: 20 mm long, mm wide. Quantity: 2 per compound leaf Shape: Linear, slightly broad based with outward extending apices. Margins: Finely serrated. Color: Yellow-Green Group 144A.

*Petiole.*—Length: 20 mm. Diameter: 2 mm.

*Upper surface.*—Color: Yellow-Green Group 144A.

*Lower surface.*—Color: Yellow-Green Group 144A.

*Rachis.*—Length: 35 to 40 mm. Upper surface: Color: Yellow-Green Group 144A.

*Lower surface.*—Color: Yellow-Green Group 144A. Observations: Small prickles.

*Leaflet.*—Quantity: Normally 5 leaflets. Margins: Serrated. Size: On average terminal leaflets are 40 mm long, 23 mm wide. Shape: Generally elliptical. Base: Rounded. Apex: Cuspidate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Climbing rose class named 'Poulcy028', substantially as illustrated and described herein, due to its abundant yellow flowers, disease resistance, and extended period of bloom.

* * * * *

'Poulcy028'